United States Patent [19]

Tsurumizu et al.

[11] Patent Number: 4,731,245
[45] Date of Patent: Mar. 15, 1988

[54] **VACCINE, ANTIGEN AND ANTIBODY FOR TREATING MICROORGANISMS OF THE MCLS-TYPE *STREPTOCOCCUS SANGUIS***

[75] Inventors: Takashi Tsurumizu, Ichikawa; Takashi Hashimoto, Chofu; Makoto Sato, Tokushima, all of Japan

[73] Assignee: Kitasato Kenkyusho, Japan

[21] Appl. No.: 758,576

[22] Filed: Jul. 24, 1985

Related U.S. Application Data

[63] Continuation-in-part of Ser. No. 686,347, Dec. 26, 1984, abandoned.

[30] Foreign Application Priority Data

Dec. 29, 1983 [JP] Japan .................. 58-251976
Jun. 21, 1985 [JP] Japan .................. 60-135416

[51] Int. Cl.$^4$ .................. A61K 39/09; A61K 39/395
[52] U.S. Cl. .................. 424/92; 424/85; 424/87; 424/88; 530/387; 435/68; 435/885
[58] Field of Search .................. 424/88, 85, 87, 92; 435/253, 885, 68; 530/387

[56] References Cited

U.S. PATENT DOCUMENTS 3,931,378 1/1976 Gaffar et al. .................. 424/92
4,353,891 10/1982 Guggenheim et al. .................. 435/885
4,454,109 6/1984 Gillman .................. 424/50

OTHER PUBLICATIONS

Jordon et al., *Lonuts*, 1983, 1(8330), p. 931.
Krensky et al., Streptococcal Antigencity of MCLS and Rydrophic Gallbladder, *Pediatrics*, [Letter], 64(6), p. 929 (1979).
Marens, Thought on Kawasaki Disease Etiology [editorial], JAMA, 241(4), p. 399 (1979).

*Primary Examiner*—John Kight
*Assistant Examiner*—Garnette D. Draper
*Attorney, Agent, or Firm*—Wolder, Gross & Yavner

[57] ABSTRACT

A vaccine, comprising as antigen, at least a part of the cell of strains of *Streptococcus sanguis* having a high pathogenic potential and capable of decomposing raffinose and mellibiose, in association with a pharmaceutically acceptable carrier or excipient. Preferably, the antigen is derived from the pili-like structures on the surface layer of the cells. Antibodies produced by immunizing a mammal with said antigen to produce the corresponding antibodies in the body of said mammal and recovering the resultant antibodies from the mammal. A pharmaceutical composition, comprising as active ingredient said antibodies, in association with a pharmaceutically acceptable carrier or excipient. Said vaccine, antibodies and antibody-containing composition may be used for treating human and animal diseases caused or aggravated by said microorganisms such as MCLS. Preferably, the composition comprises antibodies produced by the use of antigen(s) derived from the pili-like structures, in association with a carrier or excipient suitable for oral administration. The preferred composition may be directly and safely administered to the oral cavity of humans and animals to prevent or at least inhibit the infection of the virullent strains with good results.

8 Claims, No Drawings

VACCINE, ANTIGEN AND ANTIBODY FOR TREATING MICROORGANISMS OF THE MCLS-TYPE *STREPTOCOCCUS SANGUIS*

RELATED APPLICATION

This application is a continuation-in-part of U.S. patent application Ser. No. 686,347 filed on Dec. 26, 1984 now abandoned.

BACKGROUND OF THE INVENTION

This invention relates to antigens, antibodies and antibody-containing compositions for treating human diseases such as Kawasaki disease.

Kawasaki disease which is also designated as acute febrile mucocutaneous-lymphnode-syndrome (hereinafter referred to as MCLS) is a human disease (particularly, up to 3 year old infants) reported in Japan by Kawasaki et al in 1967. Even though MCLS is similar to scarlet fever caused by hemolytic streptocci such as *Streptococcus pyogens*, MCLS is clearly distinguished from scarlet fever in that MCLS seizes the coronary artery to induce artery aneurysm. The patients of MCLS are sometimes killed by myocardinal infarction. Scarlet fever induces nephritis. Recently, public interst in MCLS has gradually increased with respect to its very high death rate of greater than about 30%. MCLS has also been reported in other countries such as the United States and Korea as well as Japan.

Various etiological factors of MCLS such as, for example, hemolytic streptococci, mites (Acarina), heavy metals, viruses and the like have hitherto been reported. However, none of them is believed to be reasonable.

On the other hand, *Streptococcus sanguis* is a known oral bacillus which produce water-soluble and insoluble dextran-like polysaccharides from sucrose. Although its acid production is similar to that of *S. mutans*, *S. sanguis* is distinguished from *S. mutans* due to the fact that *S. sanguis* decomposes sorbitol and mannitol and that the cariogenic potential of *S. sanguis* is very weak in comparison with the cariogenic potential of *S. mutans*.

PRIOR ART

White and Niven isolated *S. sanguis* from the blood of the patients of the subacute bacterial endocarditis and reported that *S. sanguis* is a kind of the socalled Viridans streptococci (J. Bact., 51:717-722, 1946).

U.S. Pat. No. 3,931,398 discloses a dental vaccine, comprising as active ingredient a purified fraction of polyfructan or polyglucan produced from sugars by the metabolic action of *S. sanguis*.

Mitsuo Torii, a Japanese researcher, has investigated 113 strains of *S. sanguis* isolated from dental plaque of humans and has reported:

(a) all strains are capable of producing glucans and hydrogen peroxide and their hemolytic activity is α-type; and (b) biologically, *S. sanguis* may be classified into A and B types. A type is capable of decomposing salicin and inulin and also capable of hydrolyzing arginine and aesculin, while B type does not exhibit such characteristics (J. of Fundamental Dentistry, 20: 341-349, 1978 in Japanese version).

In short, the etilogical relationship between MCLS and *S. sanguis* has never been reported in the art.

The present invention is based upon the discovery that a significant etiological relationship exists between strains of *S. sanguis* which have never been isolated from the patients of MCLS and Purpura (designated by us as MCLS type *S. sanguis*) and MCLS and Purpura. The antigens derived from MCLS type strains of *S. sanguis* (as hereinbefore defined) and antibodies thereto may be used for treating human diseases caused or aggravated by MCLS type strains of *S. sanguis* with good results.

SUMMARY OF THE INVENTION

In one aspect of the present invention, a vaccine for treating human diseases caused or aggravated by MCLS type strains of *Streptococcus sanguis* is provided, which comprises as active ingredient an antigen derived from at least one member selected from at least a part of the cell of said strain and culture thereof, in association with a pharmaceutically acceptable carrier or excipient.

According to another feature of the present invention, a process is provided for producing an antibody for treating said human diseases, which comprises immunizing a mammal with an antigen derived from at least one member one member selected from at least a part of the cell of said MCLS type strain and culture thereof to produce the corresponding antibodies in the body of said mammal, and recovering the resultant antibodies from the mammal.

The present invention further provides a composition for treating said diseases, comprising as active ingredient one member selected from the antigens and antibodies thereto (as hereinbefore defined) in association with a pharmaceutically acceptable carrier or excipient.

Both the vaccines and antibodies of this invention may be used for treating said human diseases effectively. The term "treating" used herein denotes doing everything needed for prevention, inhibition, curing and/or diagnosis of the human diseases as hereinbefore defined.

MCLS type strains of *S. sanguis* are clearly different from known strains of *S. sanguis*. For example, their pathogenic potential is very high and their serotypes are unique. However, they may be simply identified by the fact that they are capable of decomposing raffinose and mellibiose, with reference to the following Table 2. Also, the following Table 1 clearly indicates that MCLS type strains may be classified into two types (designated by us as MCLS1 and MCLS2 types) with respect to their antigenic characteristics.

The etiological relationship between MCLS type strains and MCLS and Purpura is exemplified as follows:

(1) In one experiment, dental plaque was collected from each member of 45 pairs of humans, each pair consisting of a patient of acute MCLS and his or her mother. Each sample was cultured at 37° C. for 48 hours on Mitis-salivarius agar plate medium (Difico., U.S.A.) and TYC agar plate medium (Arch. Oral Biol., 12, 1911-1201, 1967). After completion of culturing, the cultured broth was left at room temperature for 24 hours and the grown colonies were examined. It was found that almost all colonies were occupied mainly by *S. sanguis* and the numbers of other bacilli usually present in the oral cavity of humans were few. Small numbers of *S. salivarius* and *S. mutans* were found in several colonies.

(2) Rabbits were immunized with antigens (each 0.1 ml) derived from strains of *S. sanguis* ATCC 10556 (serotype I), ATCC 10557 (serotype II), ATCC 10558

(serotype III) and ST-7 (serotype IV), all being well recognized reference strains of *S. sanguis*, to obtain rabbit antiserums. Similarly, test antigens were prepared from MCLS type strains isolated from the above-mentioned 45 pairs of humans. The resultant antiserums and antigens were subjected to the double diffusion test to observe that all antiserums were unreactive with the test antigens.

Then, a similar test was carried out by using antiserums originating from the MCLS type strains isolated from said 45 pairs of humans to observe that MCLS type strains may be classified into two serotypes which are different from the known serotypes of *S. sanguis*. In this test, the antigens used were prepared by the Hamada's method (Infect. Immun. 14:903–910, 1976 in Japanese version). The test results are shown in the following Table 1.

TABLE 1

| Antiserum→<br>Antigen | 10556 | 10557 | 10558 | ST-7 | MCLS 1 | MCLS 2 |
|---|---|---|---|---|---|---|
| 10556 | + | − | − | − | − | − |
| 10557 | − | + | − | − | − | − |
| 10558 | − | − | + | − | − | − |
| ST-7 | − | − | − | + | − | − |
| MCLS 1 | − | − | − | − | + | − |
| MCLS 2 | − | − | − | − | − | + |

It is said that strains of *S. sanguis* are more or less similar to strains of *Streptococcus mitis*. In order to distinguish MCLS type strains of *S. sanguis* from *S. mitis*, a further test was carried out in a similar manner to that described above by the use of *S. mitis* ATCC 9811, ATCC 9895, ATCC 15910, ATCC 15911 and ATCC 15912, all being well-recognized reference strains of *S. mitis*. It has been found that both the antigens derived from the strains of *S. sanguis* ATCC 10556, ATCC 10557, ATCC 10558, ST-7, all being well-recognized reference strains of *S. sanguis* as well as the antigens derived from *S. sanguis* SHH83 (FERM P7372; MCLS 1 type) and *S. sanguis* MCLS 2 (FERM P 8169;MCLS2 type) were unreactive with all antiserums derived from strains of *S. mitis*. From these facts, it is apparent that MCLS type strains are different from *S. mitis*.

(3) Comparison of the biological characteristics of MCLS type strains isolated from said 45 pairs of humans with those of the known strains of *S. sanguis*:

TABLE 2

| | Strain type | | |
|---|---|---|---|
| | Known | | MLCS |
| | Biotype | | |
| | A | B | B |
| | Serotype | | |
| | I | II | ** |
| Production of glucans | + | + | + | |
| Hemolysis | + | + | +++ | (α-type) |
| Production of H$_2$O | + | + | + | |
| Decomposition of sugars | | | | |
| salicin | + | − | − |
| mannitol | − | − | − |
| sorbitol | − | − | − |
| raffinose* | + | − | + |
| mellibiose* | − | − | + |
| cellobiose* | | | − |
| aesculin* | + | − | − |
| inulin | + | − | − |
| Hydrolysis of arginine | + | − | − |

TABLE 2-continued

| | Strain type | | |
|---|---|---|---|
| | Known | | MLCS |
| | Biotype | | |
| | A | B | B |
| | Serotype | | |
| | I | II | ** |
| Hydrolysis of aesculin | + | − | − |

Notes:-
**Different from the known serotypes of *S. sanguis*.
Source: Mitsuo Torii, J. of Fundamental Dentistry, 20: 341–349, 1978 except marked with * (Hamada, Microbiol. Rev., 44, 331–385, 1980), both in Japanese version.

(4) The following Table 3 indicates that MCLS type strains of *S. sanguis* are living in the oral cavity of the test humans (the patients of MCLS and their mothers) at the rate of more than about 80%.

TABLE 3

| Members | Hosts | Type 1 | Type 2 |
|---|---|---|---|
| 120(100%) | 98(82%) | 68(57%) | 30(25%) |

It is noted in this regard that the concentration of MCLS type strains in the oral cavity of patients is at maximum in the acute phase and decreases according to the restoration of the health of the patients. Further it was found that among more than 400 pairs of infants (non-patients) and their mothers, only 11 mothers and 1 infants were hosts of MCLS type strains of *S. sanguis*. These facts suggest that the source of MCLS type strain in the oral cavity of the infants are probably their mothers.

(5) Where a cultured broth (each 0.1 ml) of a MCLS strain was abdominally or subcutaneously injected to more than 5 infants of gelbilis of the same venter in the weaning period, very strong erythema was observed over the entire abdominal area of all animals. Where a purified fraction of said cultured broth (each 0.1 ml) was injected subcutaneously to the animals at the end of the hind paw, very strong erythema and swelling were found at the inguinal lymphnode of all animals. Such acute syndromes occured about 6 hours after administration. The animals died at a very high death rate of greater than about 30%. In such cases, all syndromes were pathogenically very similar to the syndromes of human MCLS. However, it has been further found that the generation of these acute sydromes may be prevented or at least inhibited by previous administration of a vaccine (for example, 0.1 ml), comprising as active ingredient an antigen prepared by inactivating said purified fraction in conventional manner. Similar preventing or inhibiting effect was also observed by administration of human immunoglobulin derived from the patients of MCLS.

The above-mentioned findings clearly suggest the existence of an important etiological relationship between MCLS type strains of *S. sanguis* and MCLS.

(6) Recently, we have isolated MCLS type strains of *S. sanguis* from the oral cavity of patients of Purpura. The characteristics and test results of these strains are substantially the same as those of the above-mentioned MCLS type strains. Even though the etiology of Purpura has not yet been clarified, it is believed that MCLS type strains may cause or at least aggravate Purpura.

(7) It has also been found that an antigenic protein which we have isloated from the pili-like structures (known per se) on the surface of the cell wall of MCLS types strains of *S. sanguis* is capable of preventing or at least inhibiting the adherence (infection) of MCLS type strains to the suface of the teeth, mucous membrane and the like in the oral cavity of humans. The inhibited strains are present, for example, in the saliva. They do no longer grow and die in a relatively short period of time due to the loss of their residence or support medium.

The mycological characteristics of MCLS type strains are as follows:

I. Morphology: S. sanguis, 1×1 micron.

II. Growth on various media: (culturing was effected at 37° C. and at a specified pH for 48 hours under anaerobic conditions)

(1) TYC agar plate medium:

Round colonies having smooth margin. In growing, colonies grow down into and adhere to the medium plate.

(2) Mitis-salivarius medium (Difco., U.S.A.):

Grayish blue or dark blue colonies having the same characteristics as above.

(3) Todd Hewitt Broth agar medium (Baltimore Biological Laboratories, Inc., U.S.A., hereinafter referred to as BBL.):

Colonies are round, flat, somewhat opaque, bright somewhat mucoid and small.

(4) Tryptocase Soy Broth (BBL.):

Growing from the lower layer of the medium.

III. Physiological characteristics:

(1) Production of glucans: positive, when determined by culturing at 37° C. for 48 hours using Todd Hewitt Broth (BBL) containing sucrose (5%) and adding an equal amount of ethanol to the cultured broth.

(2) Formation of pigment: negative.

(3) Growth range: pH=3.5-8.5, Temp.=10°-39° C.

(4) Decomposition of sugars: Cf. Table 2.

Positive to glucose, galactose, maltose, sucrose, lactose, mellibiose, raffinose.

Negative to sorbitol, mannitol, salicin, aesculin, cellobiose.

IV. Miscelleneous:

Hydrolysis of aesculin and hydrolysis of arginine: negative.

Hemolysis: Human, horse, sheep . . . positive (α), determined by using a Tryptocase Soy Broth agar plate medium (BBL.) containing a defibrinated blood obtained from the sample at a concentration of 10%.

Pathogenic potential: very strong. Other characteristics are the same as those of the known strains of S. sanguis.

Strains which may be used for the purpose of this invention may be cultured in conventional manner used for culturing other strains of S. sanguis. Thus, the culturing may be effected under aerobic conditions, although aerobic culturing may, if desired, be possible. Although both organic and synthetic media may be used, liquid media may be preferred for mass propagation. Usually, culturing may be effected at a pH of 5.0-9.0 (e.g. about 7.0) and at a temperature of 20°-39° C .(e.g. about 37° C.) for 24-72 hours.

Examples of the preferred media include the following medium A:

Polypeptone 1.7%; polypeptone S (Difco., U.S.A.) 0.3%; yeast extract 0.5%; potassium phosphate, dibasic 0.25%; sodium chloride 0.5%; glucose 0.25%. (pH 7.0-7.8).

Preferred examples of the antigens and vaccines of the present invention are as follows:

(1) PLS vaccine (antigen):

A vaccine comprising as active ingredient, an antigen derived from the pili-like structures (known per se) on the surface layer of the cell wall of MCLS type strains, which may be prepared, for example, in the following manner.

After completion of culturing, the cells are separated from the cultured broth in conventional manner, for example, by centrifugation (8000 r.p.m./20 min.). The cells are suspended in a suitable hypertonic solution such as, for example, 0.2M phosphate-buffered 1M sodium chloride solution (pH 6.0-7.5). The desired antigen may be extracted from the cells, for example, with a low speed rotation (e.g. 1-5 r.p.m.) or by treating the suspension with ultrasonic waves (e.g. 10-20 KHz/5-20 min.). The extracted active material may be fractionated and purified in conventional manner such as, for example, by the sole or combined use of column chromatography, isoelectric focussing precipitation, fractional precipitation using cold solvent, membrane concentration, salting out using ammonium sulfate and the like. Especially good results may be obtained by the sucrose density-gradient ultracentrifugation.

The active material contained in the purified fraction may, if desired, be inactivated using a suitable inactivating agent such as, for example, formalin (0.2%), followed by removal of the inactivating agent, for example, by dialysis at low temperature (e.g. below 10° C.) against 0.75 M phosphate-buffered sodium chloride solution (pH 6.0-7.5). The residual solution is diluted with a similar buffer solution to give a protein N concentration of about 5-50 µg/ml. Aluminium hydroxide gel is added to the solution at a final concentration of aluminium of about 100 µg/ml to adsorb the PLS antigen. If desired, a suitable antiseptic agent (e.g. 0.01 w/v of thimerosal) may be added to the antigen solution. In this manner, the desired vaccine is obtained.

The antigenic protein originating from the pililike structures has a molecular weight of about $2-5\times10^5$. In order to obviate the denaturing of the antigen, all process steps are carried out at a low temperature of below 56° C., for example, below 10° C.).

The PLS antigen may be administered to humans, for example, at a dose of about 0.1-0.5 ml/once by subcutaneous or intramsclular injection (for example, under the skin of the mucous membrane in the oral cavity). Immunization may be effected, if desired, several times, for example, twice with an interval of 2-3 weeks.

(2) Whole cell antigen:

The cells are separated from a cultured broth of MCLS type strain in conventional manner, for example, by centrifugation (8000 r.p.m./20 min.) and washed several times, for example, with 0.6-1.5% (e.g. 0.9%) sodium chloride solution (pH about 7.0). The cells are suspended in a similar sodium chloride solution and inactivated by irradiation of ultraviolet rays. The inactivated cells are divided into small fractions and put into ampoules, followed by freeze-drying. The concentration of the cells is adjusted so that the optical density of the cell suspension is 0.5 at 550 nm when diluted with 0.9% sodium chloride solution (pH 7.0).

(3) Heat-treated antigen:

The cells separated from the cultured broth of MCLS type strain are washed with a sodium chloride solution, (e.g. 0.9%; pH 7.0) several times, followed by freeze-drying. The freeze-dried cells are suspended in a similar sodium chloride solution in an amount of about 20 mg/ml and treated at about 115°-130° C. for 15-30 minutes (e.g. at 120° C. for 20 minutes). The boiled solution is cooled and centrifuged (for example, 8000 r.p.m./20min.) to obtain the desired antigen solution as the supernatant.

(4) Extracellular antigen:

A suitable metallic salt such as, for example, 10% zinc chloride solution is added with stirring to the supernatant of a cultured broth of MCLS type strain to a final concentration of 1%. After adjusting the pH of the solution to about 6.0, the solution is allowed to stand at a low temperature, for example 4° C., to precipitate the active material. After removal of the supernatant, the precipitated fraction is collected by centrifugation (for example, 8000 r.p.m./5 min.). Crystals of ammonium sulfate (12 $H_2O$) are added to a ratio of 1/50–1/200 of the initial amount of the cultured broth. The solution is stirred and a glass filter is used to remove the by-produced zinc phosphate. The solution is then dialyzed at a low temperature (e.g. 4° C.) against 0.75M phosphate-buffered sodium chloride solution (pH about 7.0). Ammonium sulfate is added to the residual solution at a saturation of 30–60% to recover the active material. The mixture is put in a cellophane tube and dialyzed against a similar phosphate-buffered sodium chloride solution to remove ammonium sulfate.

For use, the antigen solution is diluted, for example, with 0.75M phosphate-buffered sodium chloride solution (pH about 7.0) to give a protein N concentration of about 100–200 μg/ml.

In general, these antigen solutions may preferably be used for diagnosis, for example, for the preparation of control antiserums and for determination of human serum since PLS vaccine is especially preferred for direct administration to humans due to its simplicity and safety. If desired, PLS vaccine may also be used for the foregoing purpose.

In use, the PLS vaccine and other antigen solutions may be admixed with a suitable adjuvant and injected into humans and mammals, for example, at a dose of 0.1–0.5 ml/oz in conventional manner. It is possible to immunize humans and animals two or more times. As mammals to be immunized, for example, rat, mouse, geblis, guinea pig, rabbit, horse and the like may be used.

(5) Anti-PLS antigen antibody:

A purified fraction of the solution containing PLS antigen is diluted, for example, with 0.75M phosphate-buffered sodium chloride solution (pH about 7.0) to give a protein N concentration of 10–100 μg/ml, to which is added alminium hydroxide gel at a final concentration of alminium of 100–500 μg/ml to adsorb the antigen. By immunizing a mammal, corresponding antibodies are produced in the body of the mammal. The antibodies may recovered from the mammal in conventional manner to obtain a plasma which may, if desired, be further purified. The resultant plasma or antiserum may be freeze-dried and preserved at cold temperature over an extended period of time.

The resultant antibody mainly consists of IgA and may be used for treating human diseases caused or aggravated by MCLS type strains of S. sanguis in conventional manner.

(6) Anti-PLS-antibody-containing composition:

The composition comprises the antibody to the PLS antigen as set forth, as the active ingredient in association with a pharmaceutically acceptable carrier or excipient. The composition may preferably take the forms suitable for oral administration. Advantageously, the composition may be formulated in dosage unit form.

The amount of the active ingredient contained in each dosage unit may be adjusted so as to enable the administration of the antibody at a daily dose of, for example, 1–10 units (as hereinafter defined).

Preferred examples of the compositon include gargles, dentifrices, chewing gums, lozenge and the like. Various liquid, semi-solid or solid carriers and excipients suitable for oral administration are well known in the art. Thus, suitable carriers for liquid composition are exemplified by sterile water, sodium chloride solution and armond oil, and suitable excipients for solid composition are exemplified by magnesium stearate, CMC (sodium salt), ethylparaffin, glucose and the like.

As there are two strain type, the vaccines (antigen solutions) may contain at least one antigen derived from MCLS 1 or MCLS 2 type strains of S. sanguis. Also, two types of the antibodies to these antigens may be used solely or in combination.

MCLS 1 and 2 types strains of S. sanguis are respectively exemplified by S. sanguis SSH83 (FERM-P 7372) and MCLS 2 (FERM P-8169) which have now been isolated from the oral cavity of patients of MCLS. These strain are likely to be very similar to the virulent strains of S. sanguis which have very recently been isolated from the patients of Purpura.

According to the present invention, human diseases caused or aggravated by MCLS type strains of S. sanguis may be treated (as hereinbefore defined) with good results.

In this specification, the antibody titre is expressed by the unit of gel precipitation value determined by the double diffusion precipitation method, described by Goldman et al (Isolation and Characterization of Glial Filaments from Human Brain, J. Cell Biol., 78, 426, 1978).

The following non-limiting examples and experiments illustrate the present invention, wherein the culturing was effected at 37° C. under anaerobic condtions.

EXAMPLE 1—Preparation of PLS vaccine

Streptococcus sanguis SSH83 (FERM-P 7372) was cultured for 24 hours by the use of the above-mentioned Medium A (1000 ml) to obtain a seed. 500 ml of the seed was then cultured for 24 hours using Medium A (45000 ml). After completion of culturing, ammonium sulfate (crystals) were added to the cultured broth with agitation at a saturation of 33%. After dissolving ammonium sulfate, the mixture was allowed to stand at 4° C. until the cells precipitated. After removal of the supernatant from the solution, the precipitated fraction was recovered by centrifugation (8000 r.p.m./10 min.). The cells were collected and densely suspended in a 0.2M phosphate-buffered 1M sodium chloride solution (pH 8.0; 450 ml). The active material was extracted from the cell suspension at 4° C. for 72 hours with rotation (1–5 r./min.). After this, the cells were removed from the suspension by centrifugation (8000 r.p.m./20 min.). To the supernatant were added crystals of ammonium sulfate at a saturation of 60% and ammonium sulfate was dissolved with agitation. Then, the mixture was allowed to stand at 4° C. to form precipitates. After removal of the supernatant, the precipitated fraction was recovered by centrifugation (8000 r.p.m./20 min.) and were densely suspended in a 0.2M phosphate-buffered 1M sodium chloride solution (pH 8.0; about 100 ml). The suspension was dialyzed against a similar buffer solution of more than 5000 ml (4° C.; 48 hours). The residual solution was centrifuged (8000 r.p.m./20 min.) to remove impurities. About 175 ml of the supernatant was recovered, which contained about 8000 μg/ml of protein N. The supernatant was diluted with a similar buffer solution to give a concentration of protein N of 200 μg/ml. 200 ml of the diluted solution was subjected to sucrose density-gradient ultracentrifugation by the use of Hitachi 65P Ultracentrifuge with a zonal rotor RP 235 T (commercial product of Hitachi Limited, Tokyo; sucrose density . . . 5–30%; 35000 r.p.m./18 hours). The desired PLS antigen was found in the fractions at a sucrose density of about 10–15%, the concentration of protein N in the desired active fractions being about 42–50 μg/ml. The active fractions were collected, combined and inactivated at 4° C. for 14 days with addition of formalin(0.2%), followed by dialysis at 4° C. against 0.75M phsophate-buffered sodium chloride solution (pH 7.0; 5000 ml) to remove unreacted formalin. The inactivated solution was diluted with 0.75M phosphate-buffered sodium chloride solution (pH 6.2–6.5) to give a protein N concentration of 5–10 μg/ml. To this solution was added aluminium hydroxide gel at a final concentration of aluminium of 100 μg/ml to adsorb the desired antigen, followed by addition of thimerosal (antiseptic agent; 0.01% w/v).

EXAMPLE 2—Preparation of mixed vaccine

*Streptococcus sanguis* MCLS 2 (FERM-P 8169) was treated in a similar manner to that described in Example 1. The inactivated solution thus-obtained and the inactivated antigen solution obtained by the method of Example 1 were mixed together, each solution containing 10 μg/ml of protein N. Aluminium hydroxide gel was added to the mixture to a final concentration of aluminium of 100 μg/ml to adsorb the antigens. Finally, thimerosal (0.01 w/v) was added to the antigen solution to obtain the desired mixed vaccine.

EXAMPLE 3—Preparation of extracellular antigen solution

10% zinc chloride solution was added to the supernatant of the cultured broth described in Example 1 at a final concentration of zinc chloride of 1% with agitation. The pH of the mixture was adjusted to 6.0, and the mixture was allowed to stand at 4° C. to precipitate the active material. After removal of supernatant, the precipitated fraction was recovered by centrifugation (8000 r.p.m./5 min.), to which were then added crystals of disodium phosphate (12 H₂O) in an amount of 1/50–1/200 of the initial cultured broth while stirring. A glass filter was used to remove the by-produced zinc phosphate. The rest was dialyzed at 4° C. against 0.75M phosphate-buffered sodium chloride solution (pH 7.0). To the residual solution was added ammonium sulfate at a saturation of 60% to recover the active material. The mixture was dialyzed at 4° C. against a similar phosphate-buffered solution to remove ammonium sulfate to obtain a desired antigen solution (about 200 ml).

EXAMPLE 4—Preparation of anti-PLS antigen antiserum

A PLS antigen solution (5 ml) prepared in a similar manner to that described in Example 1 was mixed with Freund's complete adjuvant (5 ml; Difco., U.S.A.). The mixture (0. 1 ml in total) was injected into a rabbit having a body weight of 3 kg at 10 places on the back of the animal. The animal was bred for one month and killed by cardiac puncture. Blood was collected from the animal and treated with a saturated ammonium sulfate (33%) in conventional manner, followed by dialysis at 4° C. in a similar manner to that described in the foregoing example to remove ammonium sulfate. About 60–80 ml of the desired antiserum was obtained per rabbit.

EXAMPLE 5—Antibody-containing composition (dental paste)

A dental paste was prepared in a conventional manner by adding an antibody to a mixture of calcium hydrogen phosphate (60%; fine powders), glycerol (30%), CMC (Na-salt; 10%) and parabens (0.25%; antiseptic agent). The antibody was prepared by the method of Example 4 and the titre of the antibody in the mixture was adjusted to 4 units (as hereinbefore defined) per 50 g of the product.

EXPERIMENTS

In the following experiments, *S. sanguis* SSH83 (FERM-P 7372; MCLS 1 type strain) was used, otherwise specified, although similar results were obtained by the use of *S. sanguis* MCLS2 (FERM-P 8169; MCLS2 type strain). In Experiments 1–3, infants of gelbis in the weaning period were used as test animals, each group of the animals consisting more than 5 children of the same venter.

EXPERIMENT 1

Mothers of the animals were respectively immunized before pregnancy by subctaneous injection of a PLS vaccine (each 0.2 ml/once) prepared by the method of Example 1, the immunization being effected twice with an interval of 2 weeks. 10 days after birth, each animal was immunized once by subcutaneous injection of the same vaccine (each 0.2 ml). The mothers and children of the control group were not immunized. *Streptococcus sanguis* SSH83 (FERM-P 7372) was cultured at 37° C. for 24 hours by using Todd Hewitt Broth (BBL.,U.S.A.). Beginning 7 days after birth, the cultured broth containing about $10^8$ living cells/ml was orally administered to each animal of all groups at a daily dose of 0.1–0.2 ml. The administration was continued for 7 days. After weaning, each animal was bred with a cariogenic diet (Diet 2000, commercial product of Funabashi Nojo, Japan) and deionized water ad libitum. After administration of the cultured broth, samples were periodically collected from the oral cavity of each animal. Each sample was cultured at 37° C. for 24 hours by using TYC agar plate medium to investigate the change of the concentration of *S. sanguis* SSH83 in the oral floras. The test period was 30 days. The results are shown in the following Table 4.

TABLE 4

| Group | Increase (%) | Number of the infected animals | | | |
|---|---|---|---|---|---|
| | | 14 | 21 | 27 | 34 |
| | | days after infection | | | |
| Immun 1 (6**) | 15.2 | 1 | 1 | 0 | 0 |
| | | 16.7% | 16.7% | | |
| Immun 2 (7**) | 15.6 | 0 | 0 | 0 | 0 |
| Untr 1 (6**) | 14.8 | 5 | 5 | 2 | 1 |
| | | 83.3% | 83.3% | 33.3% | 16.7% |
| Untr.2 (5**) | 14.4 | 3 | 2 | 2 | 2 |
| | | 60% | 40% | 40% | 40% |

Notes:-
Immun . . . immunized group; untr . . . untreated group;
Increase . . . increased body weight (%);

EXPERIMENT 2

A similar experiment to that described in Experiment 1 was carried out except the use of *S. sanguis* MCLS 2 (FERM-P 8169) to obtain the results shown in the following Table 5, from which the inhibiting activity of PLS vaccine is apparent.

TABLE 5

| Group | Increase (%) | Number of the infected animals | | | |
|---|---|---|---|---|---|
| | | 14 | 21 | 27 | 34 |
| | | days after infection | | | |
| Immun. 1 (7**) | 16.1 | 1 14.3% | 0 | 0 | 0 |
| Immun 2 (7**) | 15.7 | 0 | 1 14.3% | 0 | 0 |
| Untr. (8**) | 15.9 | 7 87.5% | 4 50% | 5 62.5% | 3 37.5% |

Notes:-Cf. Table 4

With reference to Tables 4 and 5, it has been found that PLS vaccines of the present invention are capable of effectively inhibiting the adherence of MCLS type strains to the teeth of animals, while the untreated animals exhibited a high adhering rate of more than 40% during the entire test period. Other experiments were carried out in a similar manner to that described above except the infection was effected 10 days after birth. The resultant inhibition rate was slightly lower.

In further experiments, PLS vaccines were administered after adherence of *S. sanguis* SSH83 or MCLS 2. The adhering rate was drastically reduced and the virulent strains disappeared from the oral cavity of the animals in a relatively short period of time, while the untreated animals had an adhering rate of about 40%.

EXPERIMENT 3

Dental paste prepared by the method of Example 5 was applied to 4 pairs of humans, each pair consisting of an infant (host of *S. sanguis* SSH83) and his or her mother. The dental paste was applied everyday twice in the morning and after dinner at a dose of 1 gram/once. During the test period, dental plaque was collected from each member every week. The plaque was cultured on Mitis-salivarius agar plate medium (Difco., U.S.A.) and TYC agar plate medium at 37° C. for 48 hours under anaerobic conditions to investigate the change of the virulent strain in the oral cavity of the hosts. The results are shown in the following Table 6.

TABLE 6

| Host | 1 | 2 | 3 | Host | 1 | 2 | 3 |
|---|---|---|---|---|---|---|---|
| C1 | + | − | − | M1 | + | + | − |
| C2 | − | − | − | M2 | − | − | − |
| C3 | − | − | − | M3 | + | − | − |
| C4 | − | − | − | M4 | − | + | − |

Notes:-
All members were positive after the beginning of administration and negative 4-8 weeks after the beginning of administration. The test period was 8 weeks.

We claim:

1. A vaccine for the treatment of the microorganisms MCLS-type *Streptococcus sanguis* in the oral cavity of an animal subject, said microorganism having a high pathogenic potential and capable of decomposing raffinose and mellibiose, which comprises as active ingredient or effective amount of an antigen derived from a member selected from at least a part of the cell of said microorganism and culture thereof, and a pharmaceutically acceptable carrier.

2. The vaccine of claim 1, wherein said antigen is reactive with antibodies derived from said microorganism and unreactive with antibodies derived from other microorganisms.

3. The vaccine of claim 2, wherein the microorganism is selected from *Streptococcus sanguis* SSH83 (FERM P 7372) and *Streptococcus sanguis* MCLS2 (FERM P 8169).

4. The vaccine of claim 1, wherein the antigen is derived from the pili-like structures on the surface layer of the cell wall.

5. A process for preparing antibodies for treating microorganisms of the MCLS-type *Streptococcus sanguis* in the oral cavity of an animal subject, said microorganism having a high pathogenic potential and capable of decomposing raffinose and mellibiose, which comprises immunizing a mammal with an effective amount of an antigen derived from a member selected from at least a part of the cells of said microorganism and culture thereof to produce the corresponding antibodies in the body of said mammal and recovering the resultant antibodies from said mammal.

6. The antibodies produced by the process of claim 5 in the form of antiserums.

7. A composition for the treatment of the microorganisms of the MCLS-type *Streptococcus sanguis* having a high pathogenic potential and capable of decomposing raffinose and millibiose, which comprises as active ingredient an effective amount of antibodies produced by immunizing a mammal with an effective amount of at least one antigen derived from a member selected from at least a part of the cell of said microorganisms and culture thereof to produce the corresponding antibodies in the body of said mammal recovering the resultant antibodies from said mammal, in association with a pharmaceutically acceptable carrier or excipient.

8. The composition of claim 8, wherein said antigen used to produce the antibodies at least one antigen is derived from the pili-like structures on the surface layer of the cell and said carrier or excipient is suitable for oral administration.

* * * * *